United States Patent [19]

Hirsch

[11] 4,097,534

[45] Jun. 27, 1978

[54] PROCESS FOR POLYMERIZING 4,4'-THIOBIS(6-TERT-BUTYL-M-CRESOL)

[75] Inventor: Richard H. Hirsch, St. Louis, Mo.

[73] Assignee: Monsanto Company, St. Louis, Mo.

[21] Appl. No.: 751,774

[22] Filed: Dec. 16, 1976

[51] Int. Cl.² .................................... C07C 148/00
[52] U.S. Cl. .......................................... 260/609 F
[58] Field of Search ............ 260/609 F, 47 R, 47 ET

[56] References Cited

U.S. PATENT DOCUMENTS

| | | | |
|---|---|---|---|
| 3,133,899 | 5/1964 | Kwiatek et al. | 260/609 F |
| 3,306,874 | 2/1967 | Hay | 260/47 ET |
| 3,306,875 | 2/1967 | Hay | 260/47 ET |
| 3,707,565 | 12/1972 | Hofer | 260/609 F |
| 3,749,693 | 7/1973 | Cooper | 260/47 ET |
| 3,986,981 | 10/1976 | Lyons | 260/47 UA |

*Primary Examiner*—Joseph Paul Brust
*Assistant Examiner*—Molly C. Eakin
*Attorney, Agent, or Firm*—Robert E. Wexler; George R. Beck; Edward P. Grattan

[57] ABSTRACT

A polymer of 4,4'-thiobis(6-tert-butyl-m-cresol) is prepared by contacting 4,4'-thiobis(6-tert-butyl-m-cresol) with oxygen in the presence of a copper salt/amine complex catalyst. The polymer is useful as an antioxidant for polyolefins.

13 Claims, No Drawings

PROCESS FOR POLYMERIZING 4,4'-THIOBIS(6-TERT-BUTYL-M-CRESOL)

BACKGROUND OF THE INVENTION

The compound 4,4'-thiobis(6-tert-butyl-m-cresol) is known as an antioxidant for polyolefins. Under certain conditions, however, it has been found that such compound does not confer sufficiently long-term antioxidant characteristics to polyolefins. It has also been found, however, that the polymeric form of 4,4'-thiobis(6-tert-butyl-m-cresol) provides longterm antioxidant protection to polyolefins.

It has heretofore been known to polymerize thiobisphenols, but such polymerization proceeded with the elimination of the sulfur link to produce polyphenylene ethers which do not have the antioxidant properties possessed by the thiobisphenol. In accordance with this invention, however, it has been found that the particular structure of 4,4'-thiobis(6-tert-butyl-m-cresol) can be polymerized without the elimination of sulfur. Thus, it has been found that, contrary to the teachings of the prior art, 4,4'-thiobis(6-tert-butyl-m-cresol) may be polymerized without loss of the sulfur molecule. The present process is distinguished from the prior art by the discovery that a particular specie of thiobisphenol may be polymerized to afford a product not taught or contemplated by the prior art.

PRIOR ART

The following patents are believed relevant to the process of the present invention.

U.S. Pat. No. 3,133,899 discloses the preparation of polyaryl ethers by the oxidative coupling of thiobisphenols. The oxidative coupling of 2,6-disubstituted thiobisphenols is accomplished by contacting the monomer with oxygen in an organic solvent, such as pyridine, and in the presence of a copper chloride catalyst. During the reaction, sulfur is eliminated and a linear polyphenylene ether is obtained as the product.

U.S. Pat. Nos. 3,306,874 and 3,306,875 prepare polyphenylene ethers by polymerization of 2,6-disubstituted phenols in the presence of oxygen and a copper salt/amine complex catalyst. The reaction involves a hydroxyl hydrogen of one phenol molecule with a para-hydrogen on a second phenol molecule to form the coupled ethers and/or a quinone.

U.S. Pat. No. 3,749,693 prepares polyphenylene ethers by oxidizing 2,6-disubstituted phenols in the presence of a copper salt/amine complex catalyst.

U.S. Pat. No. 3,986,981 discloses and claims polymeric thiobisphenols, including a polymer of 4,4'-thiobis(6-tert-butyl-m-cresol).

SUMMARY OF THE INVENTION

A polymer having the formula

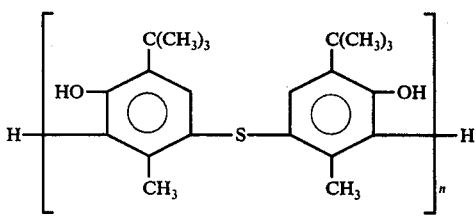

, wherein n has a value of from about 2 to 6, is afforded by reacting 4,4'-thiobis(6-tert-butyl-m-cresol) with oxygen in the presence of a copper salt/amine complex.

SPECIFIC EMBODIMENTS OF THE INVENTION

In accordance with the present invention it has been found that 4,4'-thiobis(6-tert-butyl-m-cresol) may be polymerized to a polymer containing sulfur linkages between the phenolic groups. Thus, it has been found that the sulfur linkage between the phenolic groups can be retained in the case of 4,4'-thiobis(6-tert-butyl-m-cresol) since the t-butyl group is too bulky to permit attack by the oxygen radical at the para-carbon position of the phenolic group. In order to form the polyphenyl ether by the reaction of a thiobisphenol with oxygen, attack by oxygen at the para-carbon position is necessary. Further, it is likely that attack at the para-carbon position is hindered by the presence of the meta-methyl group in 4,4'-thiobis(6-tert-butyl-m-cresol).

As stated above, the particular thiobisphenol which may be polymerized to afford a poly(thiobisphenol) is 4,4'-thiobis(6-tert-butyl-m-cresol). This material is reacted with oxygen in the presence of a copper salt/amine catalyst complex and an inert diluent.

Inert diluents which may be used include benzene, chlorobenzene, nitrobenzene, xylene, toluene, esters such as butyl acetate, and amines. Preferably the inert diluent serves as a solvent for the copper salt/amine complex but, although the solvating properties of the diluent are a prime factor in any choice of diluent, the major purpose of the diluent is to provide a liquid phase in which the thiobisphenol and catalyst complex may interface. In some cases, an amine may be used as a solvent and serve a dual purpose in that such solvent may complex with the copper salt to form the catalyst complex utilized in the polymerization reaction.

Amines which may be utilized to form the catalyst complex include heterocyclic amines such as pyridine, cyclic amines such as cyclohexyl amine, secondary amines such as diethylamine and di-n-butylamine, primary amines such as n-butylamine, t-butylamine and t-octylamine, and tertiary amines such as tetramethylethylene diamine.

Copper salts which may be utilized in accordance with the process of this invention include cuprous chloride, cuprous bromide, cuprous sulfate, cuprous acetate, cuprous propionate, cuprous palmitate, cuprous benzoate and the analogous cupric salts.

The molar ratio of 4,4'-thiobis(6-tert-butyl-m-cresol) to oxygen may be from about 2.0 to about 3.2 but is preferably from about 2.5 to about 2.8, and especially about 2.7. The molar ratio of 4,4'-thiobis(6-tert-butyl-m-cresol) to the copper salt catalyst complex is from about 35 to about 45, preferably from about 38 to about 42 and especially about 40. The molar ratio of 4,4'-thiobis(6-tert-butyl-m-cresol) to amine is from about 40 to about 53, especially from about 45 to about 49, preferably about 47. The molar ratio of copper salt to the amine is from about 0.8 to about 1.4, preferably from about 0.9 to about 1.3 and especially about 1.2.

In a typical example, 105.7 grams (0.29 mole) of 4,4'-thiobis(6-tert-butyl-m-cresol) is reacted with 3.45 grams (0.11 mole) oxygen in the presence of 0.73 gram (7.4 mmole) cuprous chloride and 0.73 gram (6.3 mmole) tetramethylethylene diamine to afford 100 grams (0.08 mole) of the polymer having a molecular weight of 1328.

In the above exemplification, the molar ratio of 4,4'-thiobis(6-tert-butyl-m-cresol) to oxygen is 2.73 (weight ratio is 30.6), the molar ratio of 4,4'-thiobis(6-tert-butyl-m-cresol) to cuprous chloride is 39.98 (weight ratio is 144.8), the molar ratio of 4,4'-thiobis(6-tert-butyl-m-cresol) to tetramethylethylene diamine is 46.93 (weight ratio is 144.8) and the molar ratio of cuprous chloride to tetramethylethylene diamine is 1.17 (weight ratio is 1.0).

The reaction rate is principally affected by temperature, oxidant and catalyst addition.

The reaction may be conducted at temperatures ranging from about 0° C. to about 100° C. Preferably, the reaction is conducted at a temperature between about 20° and about 80° C., especially from about 50° to about 55° C. In general, increasing the reaction temperature increases the reaction rate. On the other hand, higher temperatures may contribute to product coloration.

The oxidant may be either air or oxygen. Oxygen is preferred since calculation of mole ratios and reaction monitoring is facilitated by its use. Oxygen, whether used alone or as a component of air or inert gas, is taken up quantitatively in the reaction.

The catalyst may be preformed or it may be formed in situ. Thus, the pre-formed catalyst is prepared by charging diluent, copper salt and amine and heating to reaction temperature. Thereafter, 4,4'-thiobis(6-tert-butyl-m-cresol) is charged and oxygen flow is initiated. Alternatively, the diluent, amine and 4,4'-thiobis(6-tert-butyl-m-cresol) are charged, heated to reaction temperature and then the copper salt is charged and oxygen flow is initiated. It is preferred to use catalyst which has been pre-formed since it affords faster reaction rates, especially when using oxygen as the oxidant.

The molecular weight (i.e. degree of polymerization) of the product is directly proportional to the amount of oxygen absorbed in the reaction. A polymer of any predetermined chain length may be obtained by calculating the moles of reactants to be used. Thus, in formula I, $$n = \frac{1}{1 - 2\left(\frac{\text{moles } O_2}{\text{moles thiobisphenol}}\right)}$$

The molecular weight of the product is calculated as 356.52 n. The polymeric antioxidant prepared in accordance with the process of the present invention has a molecular weight of from 713.04 to 2139.12 (i.e. n=2-6). Preferably the molecular weight is from about 900 to about 1500, especially from about 1100 to about 1400. Although n may theoretically range from about 2 to about 6, it is understood that, in practice, n may have an average value of from about 1.5 to about 10. Especially preferred is a polymer wherein n has an average value of from about 3.1 to about 4.0 and a corresponding molecular weight of from about 1100 to about 1400.

EXAMPLE

Cuprous chloride (0.1 g, 1.0 mmole) and tetramethylethylene diamine (0.1 g, 0.9 mmole) were stirred in toluene (100 g) in an oxygen atmosphere. After 30 minutes 4,4'-thiobis (6-tert-butyl-m-cresol) (14.3 g, 0.04 mole) was added in one portion and oxygen made available to the reaction mixture. When 330 cc (0.015 mole) of oxygen had reacted, 5% hydrochloric acid (50 ml) was added. The mixture was stirred for 30 minutes and the aqueous phase discarded. After a water (50 ml) wash the toluene phase was concentrated to give 13.5 g of the light yellow polymer corresponding to formula I, having a molecular weight of 1360.

What is claimed is:

1. Process for preparing a polymer of the formula

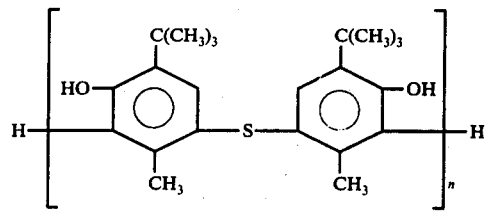

wherein n has an average value of from about 1.5 to about 10 by polymerizing 4,4'-thiobis(6-tert-butyl-m-cresol) which comprises reacting said cresol with oxygen at a molar ratio of from about 2 to about 3.2 and at a temperature of from about 20° C. to about 80° C. in the presence of a copper salt/amine complex catalyst and an inert diluent, the molar ratio of said cresol to said complex being from about 35 to about 45, the molar ratio of said cresol to said amine being from about 40 to about 53 and the molar ratio of said copper salt to said amine being from about 0.8 to about 1.4, said copper salt being selected from chloride, bromide, acetate, propionate, palmitate and benzoate, and said amine being selected from pyridine, cyclohexylamine, diethylamine, di-n-butylamine, n-butylamine, t-butylamine, t-octylamine and tetramethylethylene diamine.

2. Process of claim 1 wherein said diluent is benzene.
3. Process of claim 1 wherein said diluent is toluene.
4. Process of claim 1 wherein said copper salt is cuprous chloride.
5. Process of claim 1 wherein said copper salt is cuprous bromide.
6. Process of claim 1 wherein said amine is tetramethylethylene diamine.
7. Process of claim 1 wherein said amine is t-octylamine.
8. Process of claim 1 wherein said amine is pyridine.
9. Process of claim 1 wherein said temperature is 50° C.
10. Process of claim 1 wherein said cresol/oxygen ratio is from about 2.5 to about 2.8.
11. Process of claim 10 wherein said cresol/oxygen ratio is about 2.7.
12. Process of claim 1 wherein said catalyst is a complex of cuprous chloride and tetramethylethylene diamine.
13. Process of claim 1 wherein said catalyst is a complex of cuprous bromide and tetramethylethylene diamine.